United States Patent [19]

Ecsery et al.

[11] Patent Number: 4,564,706
[45] Date of Patent: Jan. 14, 1986

[54] PROCESS FOR THE PREPARATION OF PROPARGYL AMINES

[75] Inventors: Zoltán Ecsery; Éva Somfai; Judit Hermann née Vörös, all of Budapest; Lajos Nagy, Szentnedre; Gabor Szabo, Budapest; Otto Orban, Budapest; Laslzo Arvai, Budapest, all of Hungary

[73] Assignee: Chinoin Gyogyszer es Vegyeszeti Termekek Gyara R.T., Budapest, Hungary

[21] Appl. No.: 514,149

[22] Filed: Jul. 14, 1983

[30] Foreign Application Priority Data

Jul. 14, 1982 [HU] Hungary ................ 2278/82

[51] Int. Cl.$^4$ ............ C07C 87/28; C07C 85/04
[52] U.S. Cl. .................... 564/376; 564/374; 564/381; 564/386; 564/391
[58] Field of Search ............ 564/374, 381, 391, 376, 564/386

[56] References Cited

U.S. PATENT DOCUMENTS

| | | | |
|---|---|---|---|
| 3,397,236 | 8/1968 | Watson, Jr. .......... | 564/391 X |
| 3,429,922 | 2/1969 | Berdji et al. .......... | 564/381 |
| 3,496,195 | 2/1970 | Ecsery et al. .......... | 564/381 |
| 4,117,164 | 9/1978 | Nedelec et al. .......... | 564/386 X |
| 4,156,017 | 5/1979 | Kruger et al. .......... | 564/391 X |

OTHER PUBLICATIONS

Stoarks et al., "Phase Transfer Catalysis", pp. 1–4, 117, and 120–122, (1978).

*Primary Examiner*—Robert V. Hines
*Attorney, Agent, or Firm*—Karl F. Ross; Herbert Dubno

[57] ABSTRACT

The invention relates to a new process for the preparation of propargyl ammonium chlorides of the Formula I

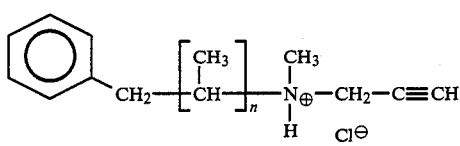
(I)

by alkaline decomposition of the d-tartarate of the 1-isomer of an amine of the Formula II

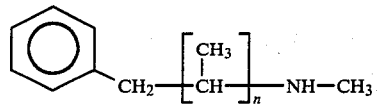
(XIIX)

and subsequent reaction of the amine of the Formula II with a halide of the Formula III $$X-CH_2-C\equiv CH \quad (III)$$

in the presence of an organic solvent, alkali and water in which in Formulae II and III respectively,
n is 1 or 0 and
X stands for halogen which comprises reacting the d-tartarate of the 1-isomer of an amine of the Formula II in aqueous suspension with an alkali, dissolving the base of the Formula II, thus set free without isolation in a water non-miscible organic solvent and reacting the same in the said phase with a halide of the Formula III, and thereafter—preferably after separating the aqueous layer—reacting the mixture which contains the amines of the Formulae II and IV

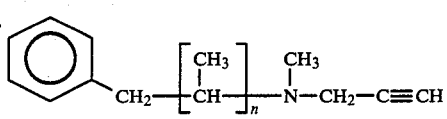
(IV)

in the organic phase in the presence of water with an organic acid or a solution which has a pH value of 1.5–6 and consists of an inorganic acid and water, thus dissolving in the two-phase mixture formed the salt of the amine of the Formula II in the aqueous layer and selectively separating the amine of the Formula II from the amine of the Formula IV, and thereafter adding after the separation of the phases hydrogen chloride to the amine of the Formula IV being in the organic phase and thus precipitating the salt of the Formula I.

The compounds of Formula I are known pharmaceutical active ingredients. The advantage of the process of the present invention that it is highly economical and enables the recovery of the starting materials on large scale production too.

6 Claims, No Drawings

PROCESS FOR THE PREPARATION OF PROPARGYL AMINES

This invention relates to a new process for the preparation of propargyl amines.

It is known that certain phenyl isopropyl amine derivatives possess valuable pharmaceutical properties and exhibit particularly useful MAO inhibiting and anti-parkinson effect.

Several methods are known for the preparation of propargyl amines. Thus a bromo allyl amine derivative can be prepared by reacting the secondary amine with 0.5 moles of bromo allyl bromide [Ann. 445, 206 (1926)]. This process is, however, complicated, lengthy, requires much labor and gives a yield of but 30–40%.

The invention relates to a new process for the preparation of propargyl ammonium chlorides of the Formula I

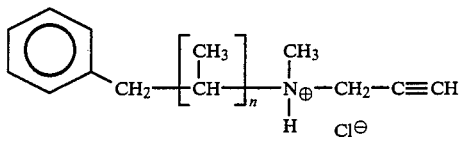

(I)

by alkaline decomposition of the d-tartarate of the l-isomer of an amine of the Formula II

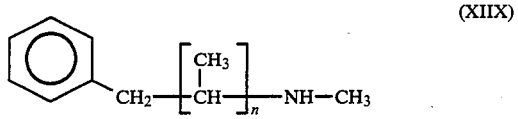

(XIIX)

and subsequent reaction of the amine of the Formula II with a halide of the Formula III $$X-CH_2-C\equiv CH \quad (III)$$

in the presence of an organic solvent, alkali and water
in which in Formulae II and III respectively
n is 1 or 0 and
X stands for halogen which comprises reacting the d-tartarate of the l-isomer of an amine of the Formula II in aqueous suspension with an alkali, dissolving the base of the Formula II, thus set free without isolation in a water non-miscible organic solvent and reacting the same in the said phase with a halide of the Formula III, and thereafter—preferably after separating the aqueous layer—reacting the mixture which contains the amines of the Formulae II and IV

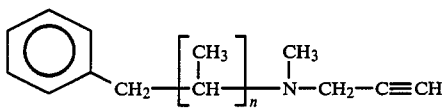

(IV)

in the organic phase in the presence of water with an organic acid or a solution which has a pH value of 1.5–6 and consists of an inorganic acid and water, thus dissolving in the two-phase mixture formed the salt of the amine of the Formula II in the aqueous layer and selectively separating the amine of the Formula II from the amine of the Formula IV, and thereafter adding after the separation of the phases alcoholic hydrogen chloride or gaseous hydrogen chloride to the amine of the Formula IV being in the organic phase and thus precipitating the salt of the Formula I.

The present invention is based on the recognition that the propargyl halide should not be used in an excess, because this leads to the formation of polymeric by-products of tarry character. This risk is particularly involved on large scale production where it is also accompanied by the irritating effect of propargyl halides rising safety problems.

The invention is further based on the recognition that the separation of the tertiary amine [e.g. N-methyl-N-(2-phenyl-1-methyl)-ethyl-N-propargyl amine] being present in the reaction mixture from the secondary amine [e.g. N-methyl-N-(2-phenyl-1-methyl)-ethyl-amine] being also present in the reaction mixture and possessing very similar properties is very difficult and causes such serious problems in the working-up of the reaction mixture which already adversely effect the proper carrying out of the reaction.

It has been found that the pKA value of the tertiary base amounts to 6.2, while that of the secondary base is 9.8. The above difference can be used for making the reaction more selective and for separating the products, respectively.

In the first step of the reaction the d-tartarate of the l-isomer of the amine of the Formula II is reacted in an aqueous suspension with an alkali and the base thus set free is dissolved without isolation in a water non-miscible organic solvent (e.g. preferably benzene, toluene, dichloroethane or diisopropyl ether).

The free base is reacted in the organic phase with a halide of the Formula III; in the said organic layer both amines of the Formulae II and IV are present. The said organic phase can be reacted with a solution which has a pH of 1.5–6 and consists of an inorganic acid and water. Thus the salt of the secondary amine formed with the added inorganic acid is obtained which goes over into the aqueous layer. An inorganic acid preferably hydrochloric acid, phosphoric acid or sulfuric acid can be used.

One may also proceed by reacting the organic layer which contains the amines of the Formulae II and IV with an organic acid in the presence of water. For this purpose preferably mono- or polycarboxylic acids can be applied (e.g. acetic acid, propionic acid, formic acid, glycolic acid and) or lactic acid. The salt of the amine of the Formula II formed with the organic carboxylic acid is obtained and dissolved in the aqueous layer. The secondary amine content of the organic phase of the two-phase mixture is decreased to such a low value that it no more effects in an adverse manner the isolation of the amine salt of the Formula I. The end-product thus obtained is suitable for direct medical use.

The reaction mixture can be preferably worked up by adding alcoholic hydrogen chloride or gaseous hydrogen chloride to the organic layer which contains the compound of the Formula IV.

The salts being present in the aqueous layer can be separated from the amines being in the organic phase on the basis of the principles of the separation of phases (e.g. sedimentation, decanting etc.).

Since the reactions are carried out in a multi-phase system, one may proceed preferably by reacting the compounds of the Formulae II and III in the presence of a phase-transfer catalyst (e.g. N-benzyl-N,N,N-triethyl-ammonium-chloride).

The propargylation reaction can be carried out advantageously at a temperature between 40° C. and 70° C.

According to a further embodiment of the process of the present invention the propargyl halide and the aqueous alkali and optionally the phase-transfer catalyst are parallelly added to the secondary amine base or a solution thereof formed with a solvent.

Further details of the present invention are to be found in the following Examples without limiting the scope of protection to the said Examples.

EXAMPLE 1

351.2 g of 1-N-methyl-(2-phenyl-1-methyl)-ethyl-amine-d-tartarate are suspended in 500 ml of water. The suspension is alkalized to the pH value of 13 by adding 700 ml. of a 40% sodium hydroxide solution at room temperature. The solution is extracted with benzene. To the extract at 60° C. 98 ml. of propargyl bromide and a solution of 46 g. of sodium hydroxide and 170 ml. of water are added. The reaction mixture is stirred at 60° C. for 2 hours, whereupon the two phases are separated. The benzene phase is washed with water. To the benzene layer a solution of 100 ml. of water and 5 ml. of acetic acid is added so that the resulting aqueous layer has a (pH 6.5–7).

If the pH value of the aqueous layer is higher than 7, a further amount of acetic acid is added and the two phases are repeatedly admixed.

Thereafter the benzene phase is separated from the aqueous layer containing the 1-N-methyl-(2-phenyl-1-methyl)-ethyl amine acetate, the organic layer is washed with water and dried.

From the benzene solution about 200 ml. of benzene are distilled off at a bath temperature of 50° C. in vacuo (200 Hgmm). The filtrate is clarified and acidified to the pH value of 1 by adding dropwise a 37% ethanolic hydrogen chloride solution. Thus 170 g of N-methyl-N-(2-phenyl-1-methyl-ethyl-N-propargyl-ammonium chloride are obtained, mp.: 141°–143° C.; $[\alpha]_D^{20} = -12°$ (c=10, water).

From the mother-lye and the washing solution a further amount (20–50 g.) of the product can be isolated.

From the acetic acid washing liquid 30 g. of 1-N-methyl-(2-phenyl-1-methyl)-ethyl-amine base are recovered which can be used in the next batch.

EXAMPLE 2

One proceeds according to Example 1 except that a solution of 121 g. of N-benzyl-N-methyl-amine in 850 ml. of benzene, 4.3 g. of N-benzyl-N,N,N-trimethyl-ammonium chloride, 84 ml. of propargyl bromide, an aqueous solution of 39 g. of sodium hydroxide in 145 ml. of water and acetic acid are used. Thus 159 g. of N-benzyl-N-methyl-propargyl-ammonium chloride are obtained.

EXAMPLE 3

From 351.2 g. of 1-N-methyl-(2-phenyl-1-methyl)-ethyl-amine-d-tartarate the base is set free with a 40% sodium hydroxide solution according to Example 1. To the base in benzene 5 g. of N-benzyl-N,N,N-triethylammonium chloride are added, whereupon at 60° C. 9.8 ml. of propargyl bromide and a solution of 46 g. of sodium hydroxide in 170 ml. of water are added. The reaction mixture is worked up as described in Example 1. Thus 167.0 g. of N-methyl-N-(2-phenyl-1-methyl-ethyl-N-propargyl-ammonium chloride are obtained.

EXAMPLE 4

One proceeds as described in Example 3 except that 351.2 g. of 1-N-methyl-(2-phenyl-1-methyl)-ethyl-amine-d-tartarate, 91.8 ml. of propargyl bromide and a solution of 46 g. of sodium hydroxide in 170 ml. of water are used. Thus the benzene solution of N-methyl-N-(2-phenyl-1-methyl)-ethyl-N-propargyl-amine is obtained.

The pH of this solution is adjusted to 6.5–7 by adding 100 ml. of 5% hydrochloric acid. If the pH of the aqueous phase is higher (pH above 7), a further amount of hydrochloric acid is added in order to adjust the pH to the desired value of 6.5–7. The benzene solution is separated and worked up as described in Example 1. Thus 155.0 g. of N-methyl-N-(2-phenyl-1-methyl)-ethyl-N-propargyl-ammonium chloride are obtained.

What we claim is:

1. A process for the preparation of a salt of the Formula (I)

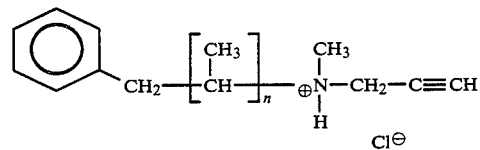

wherein n=0 or 1
which comprises the steps of:
(a) dissolving a free base of the Formula (II)

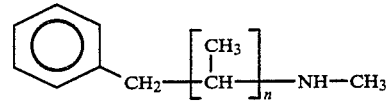

in a water, non-miscible organic solvent and propargylating said free base with a compound of the Formula (III)

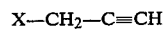

wherein X is halo, in the presence of an alkali and water at 40°–70° C. to yield a mixture of the unreacted free base of the Formula (II) and a free base of the Formula (IV)

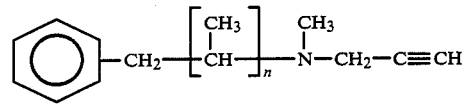

in a two-phase system containing an organic phase and a first aqueous phase;
(b) separating the organic phase which contains the mixture of the free base of the Formula (II) and the free base of the Formula (IV) from the first aqueous phase;
(c) treating the organic phase containing the mixture of the free base of the Formula (II) and the free base of the Formula (IV) with water and an amount of acid sufficient to adjust the pH of the solution to 6.5 to 7 to selectively dissolve, in a second two-phase system thus formed, a salt of the compound of the Formula (II) in the aqueous phase while the free base of the Formula (IV) remains in the organic phase;

(d) separating the aqueous phase from the organic phase; and (e) treating the organic phase containing the free base of the Formula (IV) with hydrogen chloride to precipitate the salt of the Formula (I).

2. The process defined in claim 1, wherein in step (a), the reaction of the compounds of the Formula (II) and (III) is carried out in the presence of a phase transfer catalyst.

3. The process according to claim 1, wherein in step (a), the water non-miscible organic solvent is benzene, toluene, dichloroethane, or diisopropyl ether.

4. The process defined in claim 2, wherein the phase transfer catalyst is N-benzyl-N,N,N-triethyl-ammonium chloride.

5. The process defined in claim 1, wherein in step (a), the propargylation is carried out at a temperature of 60° C.

6. A process for the preparation of a salt of the Formula (I)

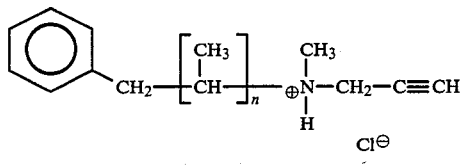

wherein $n=0$ or $1$ which comprises the steps of:

(a) alkali decomposing an aqueous suspension of the D-tartarate of the l-isomer of a compound of the Formula (II)

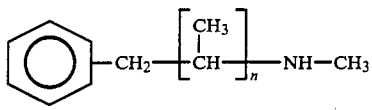

with an alkali, to obtain the free base of the Formula (II) without isolation;

(b) dissolving the free base of the Formula (II) in a water, non-miscible organic solvent and propargylating said free base with a compound of the Formula (III)

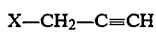

wherein X is halo, in the presence of an alkali and water at 40° to 70° C. to yield a mixture of the unreacted free base of the Formula (II) and a free base of the Formula (IV)

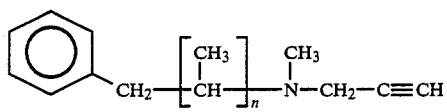

in a two-phase system containing an organic phase and a first aqueous phase;

(c) separating the organic phase which contains the mixture of the free base of the Formula (II) and the free base of the Formula (IV) from the first aqueous phase;

(d) treating the organic phase containing the mixture of the free base of the Formula (II) and the free base of the Formula (IV) with water and an amount of acid sufficient to adjust the pH of the solution to 6.5 to 7 to selectively dissolve, in a second two-phase system thus formed, a salt of the compound of the Formula (II) in the aqueous phase while the free base of the Formula (IV) remains in the organic phase;

(e) separating the aqueous phase from the organic phase; and (f) treating the organic phase containing the free base of the Formula (IV) with hydrogen chloride to precipitate the salt of the Formula (I).

* * * * *